United States Patent [19]

Hui et al.

[11] Patent Number: 5,789,213
[45] Date of Patent: Aug. 4, 1998

[54] METHOD AND COMPOSITIONS FOR HIGH EFFICIENCY LOADING, TRANSFECTION AND FUSION OF CELLS BY ELECTRIC PULSES

[75] Inventors: Sek Wen Hui, Williamsville, N.Y.; Natailia Stoicheva, Sofia, Bulgaria; Ya-Li Zhao, Buffalo, N.Y.

[73] Assignee: Health Research Inc., Buffalo, N.Y.

[21] Appl. No.: 439,187

[22] Filed: May 11, 1995

[51] Int. Cl.$^6$ .................................................. C12N 13/00
[52] U.S. Cl. ........................... 435/172.3; 435/172.2; 435/173.6; 435/173; 435/320; 435/325; 514/44
[58] Field of Search .................. 435/172.3, 172.2, 435/173, 320, 240.1, 173.6, 325; 514/44; 935/54, 71, 34

[56] References Cited

U.S. PATENT DOCUMENTS

| | | | |
|---|---|---|---|
| 4,181,589 | 1/1980 | Brooks | 204/180 R |
| 4,743,550 | 5/1988 | Ananthapadmanabhan et al. | 435/220 |
| 4,849,355 | 7/1989 | Wong | 435/172.3 |
| 5,110,733 | 5/1992 | Kim et al. | 435/183 |
| 5,232,856 | 8/1993 | Firth | 435/287 |
| 5,407,810 | 4/1995 | Builder et al. | 435/69.1 |

OTHER PUBLICATIONS

Alstine et al (Jan. 1996); Tibtech; vol. 14, Oct. 3, 1996.

*Primary Examiner*—Christopher S. F. Low
*Assistant Examiner*—Dave Nguyen
*Attorney, Agent, or Firm*—Hodgson, Russ, Andrews, Woods & Goodyear

[57] ABSTRACT

Methods and compositions are provided for use in electroloading procedures to increase the transfection and fusion efficiency compared to the methods now used in the art. The compositions comprise a two-phase polymer system containing two water soluble polymers which, when mixed, result in target cells and biological material being encapsulated into one of the polymer phases in a concentrated form. The methods of the present invention for electroloading biological material into target cells comprises mixing the biological material into one of the phases of the two-phase polymer system; mixing the target cells into either of the phases of the two-phase polymer system; mixing the phases together to form an emulsion; and exposing the emulsion to a pulsing electric field in an electroloading process.

27 Claims, 6 Drawing Sheets

METHOD AND COMPOSITIONS FOR HIGH EFFICIENCY LOADING, TRANSFECTION AND FUSION OF CELLS BY ELECTRIC PULSES

This invention was made with government support under grant GM 30969 awarded by the National Institutes of Health. The government has certain rights in the invention.

FIELD OF INVENTION

The present invention relates to a method and compositions for facilitating the transfer of biological materials such as drugs, nucleic acids, or other materials into target cells. More particularly, the invention relates to the use of a non-toxic, two phase polymer system that concentrates biological materials with the target cells, such that the materials can be introduced (loaded) into target cells with high efficiency during and after administration of an electric pulse.

BACKGROUND OF THE INVENTION

Electroporation (or electropermeation, or electroloading) is a recent and convenient technique for introducing biological materials into cells. The process involves introducing a selected biological material into target cells by applying an electric field (See for example, U.S. Pat. No. 4,849,355; and U.S. Pat. No. 5,232,856). The principle of electroporation is the application of one or several short and sufficiently strong electric pulses to a suspension or monolayer of target cells, such that some parts of the cell membrane or wall are broken down temporarily to form minute pores. Surrounding molecules of biological material then diffuse or are driven into the target cells during the time when the cell membranes remain permeable to these molecules.

The efficiency of such loading and transfection depends on electric field parameters, pulsing, recovery media, and protocols (Chang et al., 1992 *Guide to Electroporation and Electrofusion*, eds., Chang, Chassy, Saunders, and Sowers; Academic Press, Inc.). In many cases, electroporation has been reported to be more efficient than chemical and viral methods for introducing biological materials into target cells. Many cells may survive the electroporation process and recover, although a large proportion of cells may die during the process, depending on the strength and the duration of the electric pulses. Using conventional methods and compositions for electroporation, the best loading and transfecting effects usually occur when the subsequent cell viability is about 50%, thereby resulting in a transient transfection rate of about 1–10%. The steady expression of such transfection ranges from about 1 to about 10 clones per million cells. An alternative method to load cells by electric pulse is to encapsulate the biological materials in liposomes and fuse the liposomes with targeted cells by electrofusion. This method is not commonly used due to a) the low loading rate of liposomes; and b) the difficulty of liposome-cell electrofusion.

The advantage of electroloading is that the process is applicable to almost all cell types ranging from bacteria to mammalian cells, and including human tissue cells. Many cells not transfectable by chemical methods, such as by calcium phosphate or DEAE-Dextran methods, can be transfected by electroloading. Unlike methods employing chemicals and/or viral vectors, the parameters for electroloading can be varied easily and independently to optimize the yield (See for example, Kubiniec et al., 1990, *BioTechnique* 8:1).

However, a common problem in electroloading (and also in calcium phosphate and DEAE-Dextran methods) is the relative inefficiency of introducing the biological material into target cells; i.e., the amount of biological material that is inserted into cells is minimal compared to the amount used in the process. Another problem is low viability rate of cells subsequent to the electroloading process; i.e., the number of viable cells after treatment with electric pulses in the electroloading process is minimal compared to the number used in the process. These problems pose obstacles in the use of conventional transfection methods, including electroloading, for various applications. For example, for gene delivery to human cells, the supply of target cells are limited; and thus tremendous waste in cells and gene materials by the conventional methods cannot be tolerated. Reservations for the use of retroviruses as a transfection vector, for delivering biological materials into the target cells, include fear of biological contamination.

Thus, there exists a need for a method and compositions which provide a non-toxic system for concentrating the biological material with the target cells prior to electroloading, such that upon electroloading the efficiency of insertion into the target cells is much higher than that attained by conventional methods.

SUMMARY OF THE INVENTION

The invention comprises a method, and compositions used therein, which utilizes a two-phase polymer system to concentrate both the target cells, and biological materials to be loaded, into one of the two phases. By concentrating the biological materials together with the target cells, the efficiency of insertion of the biological materials into the target cells by electroloading is much higher compared to conventional methods. The simplicity, high transfection and fusion efficiency, and the general applicability are advantages of the method and compositions according to the present invention.

These and further features and advantages of the invention will be better understood from the description of the preferred embodiments when considered in relation to the figures in which:

DESCRIPTION OF THE PREFERRED EMBODIMENTS

Definitions

Figure 1:
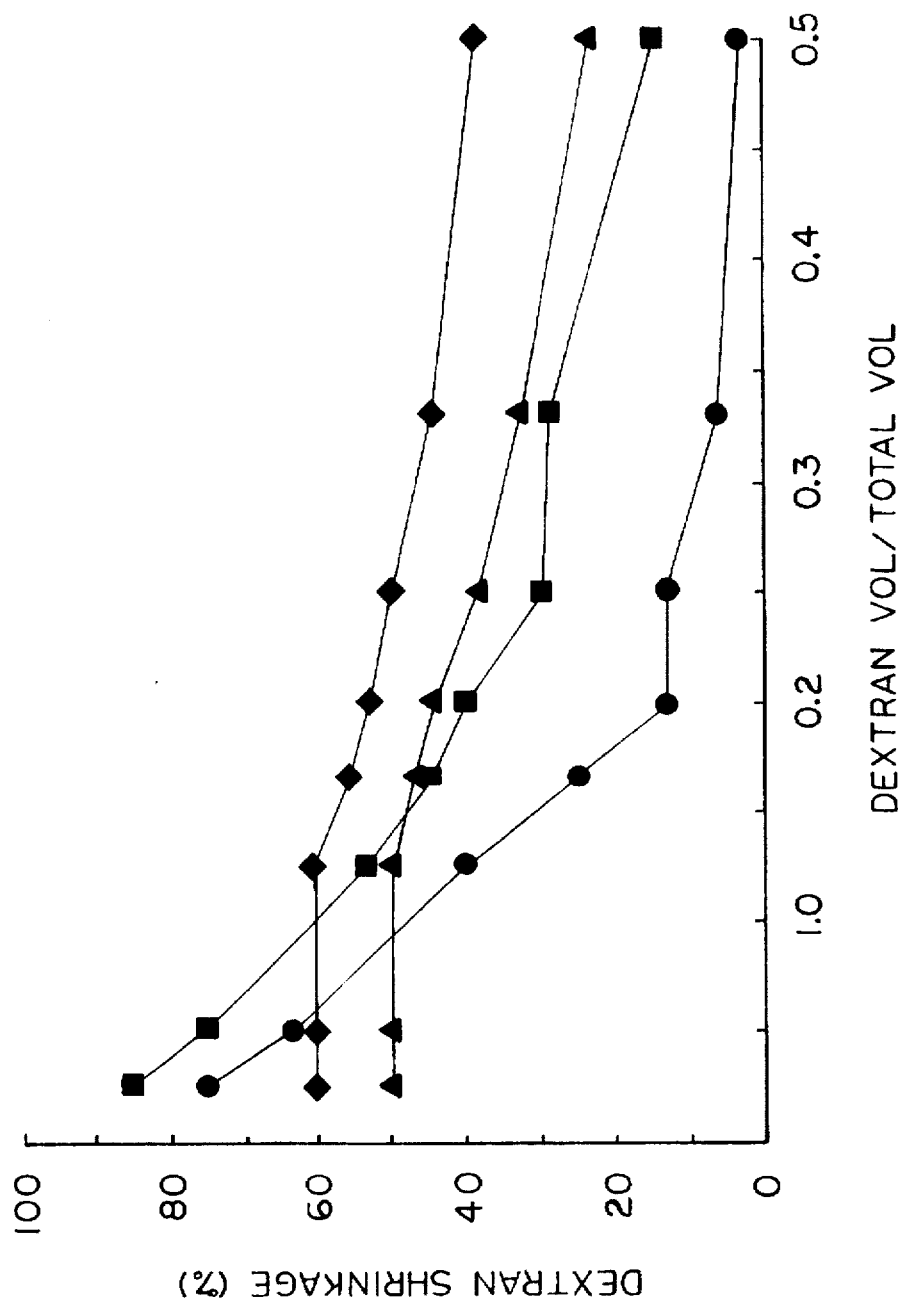
FIG. 1 is a graph showing dependence of sugar-based polymer phase shrinkage on the sugar-based polymer volume/total volume fraction. Circle, square, triangle and diamond symbols are for 10% PEG-20% dx, 10% PEG-15% dx, 20% PEG-20% dx and 20% PEG-15% dx phases, respectively (PEG-polyethylene glycol; dx-dextran).

The term "biological materials" is used herein, for purposes of the specification and claims, to mean biomolecules including, but not limited to, peptides, proteins, enzymes, polysaccharides, oligonucleotides, DNA, RNA, recombinant vectors, drugs, and dyes.

The term "target cell" is used herein, for purposes of the specification and claims, to mean the cells of choice into which the biological material is to be loaded. Depending on the application for which electroloading is performed, target cells can include either bacterial cells, animal cells, mammalian cells, or cells of human origin.

The term "electroloading" is used herein, for purposes of the specification and claims, to mean the introduction of, or loading, biological materials into target cells by either electroporation or electrofusion.

General Principles

A two-phase polymer method has been applied to separate or partition cells, proteins and minerals (See for example, U.S. Pat. No. 4,181,589; and *Partitioning in Aqueous Two-Phase Systems*, 1985, eds., H. Walter, D. Brooks, and D. Fisher, pubis. Academic Press wherein polymer concentrations are % w/w unless noted otherwise). The principle is that the partition of particles (including macromolecules) into different polymer phases depends on the interfacial energy of the particles and the polymer solutions. By varying the interfacial energy governed by the polymer and salt concentrations, selected particles (cells, macromolecules) can be driven into a given phase, hence achieving the purpose of separation or partitioning.

The method of the present invention is novel and uses combinations of polymers, which may be known in the art, which function to concentrate both target cells and biological materials into a single phase, and function to reduce the volume of this phase by osmotic control so that cells and biological materials are encapsulated in this single phase in a concentrated form during electroporation. Thus, using the compositions and method of the present invention, biological materials are driven into the target cells during electroporation, and subsequent colloidal—osmotic swelling of cells after electroporation is limited, resulting in a higher loading efficiency than conventional methods. Further, the compositions are selected for their lack of cytotoxicity, and adjusted in concentrations such that the post-pulse colloidal osmotic swelling is limited in order to reduce cell lysis, but sufficient to encourage influx of the biological material. The two-phase polymer system of the present invention may also be optimized for cell-cell and cell-liposome attachment to facilitate electrofusion as a means to introduce biological materials into cells or onto cell surfaces.

EXAMPLE 1

Characterization of the compositions

The compositions of the present invention comprise polymers which, when used in the method of the present invention, enhance the efficiency of uptake of biological materials into target cells in an electroloading process. There are several preferred characteristics for a two-phase polymer system. Typically, both polymers should be water soluble since the polymer system is used for biological samples (target cells and biological materials). Another preferred characteristic is that the polymers be substantially biocompatible since they are intimately in contact with the target cells and biological materials. A further preferred characteristic is that the polymers be relatively nontoxic since, for a limited period of time, they are intimately in contact with the target cells and biological materials. A further preferred characteristic is that, since a function of the two-phase system is to concentrate both target cells and biological materials into a single phase before electroloading, the interfacial energy and osmotic control of the two different polymer phases be such that target cells and biological materials are encapsulated in a single phase in a concentrated form for electroloading. Generally, such concentrating effect may be achieved in the two-phase polymer system by using in the two-phase polymer system one polymer having a higher osmolarity than the other polymer, resulting in shrinkage in volume of said other polymer in the two-phase polymer system. To amplify the concentrating effect, the volume of the two-phase polymer system may be adjusted so that one-fifth to one-tenth of the volume is comprised of the polymer having the lower osmolarity of the two polymers in the two-phase polymer system, with the remainder of the volume comprised of the polymer having a higher osmolarity.

In the development of the compositions and method of the present invention, various polymers and conditions were evaluated. A two-phase polymer system using polyethylene glycol (PEG; molecular size (m.w.) 8,000 (in daltons)) and one of three formulations of dextran (dx; m.w. 9,000, and 71,000 and 249,000) is illustrated in Table 1. Other two-phase systems have been developed for use in the method according to the present invention (See Table 2; concentration of polymer is noted in percent). These polymers are selected because they possess one or more of the preferred characteristics listed above. To determine if a combination of two polymers can be used in a two-phase system according to the present invention, the phase separation regions of these polymers should be determined. Phase diagrams illustrating the phase separation regions of three PEG/dx mixtures are depicted in Table 1.

TABLE 1

| Phase diagrams of PEG/dextran combinations | | | | | | |
|---|---|---|---|---|---|---|
| PEG CONC. (%) | 0 | 5 | 10 | 15 | 20 | 25 |
| dx (m.w. 71,000) | | | | | | |
| 0 | — | — | — | — | — | — |
| 5 | — | M | M | M | S | S |
| 10 | — | M | M | S | S | S |
| 15 | — | M | S | S | S | S |
| 20 | — | M | S | S | S | S |
| 25 | — | M | S | S | S | S |
| dx (m.w. 249,000) | | | | | | |
| 0 | — | — | — | — | — | — |
| 5 | — | M | M | S | S | S |
| 10 | — | M | S | S | S | S |
| 15 | — | M | S | S | S | S |

TABLE 1-continued

Phase diagrams of PEG/dextran combinations

| PEG CONC. (%) | 0 | 5 | 10 | 15 | 20 | 25 |
|---|---|---|---|---|---|---|
| 20 | — | M | S | S | S | S |
| 25 | — | M | S | S | S | S |
| dx (m.w. 9,000) | | | | | | |
| 0 | — | — | — | — | — | — |
| 5 | — | M | M | M | M | M |
| 10 | — | M | M | M | M | M |
| 15 | — | M | M | M | M | M |
| 20 | — | M | M | M | M | S |
| 25 | — | M | M | M | M | S | key:
"S" — samples in which phase separation is observed;
"M" — samples in which only a homogeneous phase is observed.

It is clear from Table 1, that within practical PEG and dextran concentrations there are phase separation regions which may be used in accordance with the present invention. In contrast, for example, the combination of PEG (m.w. 8000) and dextran (m.w. 9000) is not a combination that is desirable according to the method of the present invention because the phase separation range occurs at too high polymer concentrations (greater than or equal to 25% for each polymer). However, combinations of PEG (m.w. 8000) and dextran (m.w. 249,000), or PEG (m.w. 8000) and dextran (m.w. 71,000) are well separated systems (See Table 1) in the concentration ranges of 0% to 25%, and thus are polymer concentrations which can be used in accordance with the method of the present invention. For purposes of illustration, and not limitation, a combination comprising PEG (m.w. 8000) and dx (m.w. 71,000) for a two-phase system is used herein because of better osmotic conditions compared to a combination comprising PEG (m.w. 8000) and dextran (m.w. 249,000). The combination comprising PEG (m.w. 8000) and dx (m.w. 71,000) is hereafter referred simply as PEG/dx.

Typically, the combination useful in the method according to the present invention is a two-phase system made from a hydrocarbon-based polymer and a sugar-based polymer. Hydrocarbon-based polymers that have been found useful in the method of the present invention include various forms of PEG (m.w. range from approximately 600 to approximately 20,000); polypropylene glycol ("PPG"; m.w. of approximately 4,000); and polyacrylic acid ("PAA"; m.w. of approximately 5,000), in various concentrations. Sugar-based polymers that have been found useful in the method according to the present invention include various forms of dextran (m.w. range from approximately 9,000 to approximately 249,000); Ficoll ("Fi"; m.w. of approximately 400,000); and methyl cellulose, in various concentrations.

The first three combinations illustrated in Table 2 reflect combinations which, in addition to PEG/dx, show phase separation particularly suited to the method according to the present invention. The latter three combinations illustrated in Table 2 can be used marginally in the method according to the present invention. Phase diagrams have been constructed, and biocompatibility has been tested, for these combinations. Cells suspended in a two-phase system of either PPG/Fi or PAA/Fi appear morphologically similar to cells suspended in PEG/dx. When suspended in such two-phase systems, cells and most biological materials (with the exception of some synthetic peptides) partition favorably to, and are concentrated in, the sugar polymer phase in accordance with the present invention. Concentration of both the target cells and the biological materials to one phase is the condition for enhanced uptake to occur during the electroporation process. Both the PPG/Fi an the PAA/Fi two-phase polymer systems, with careful parameter optimization, appear to effect similar results in electroloading when compared to use of PEG/dx.

TABLE 2

Exemplary two-phase systems

20% PEG/20% Fi
100% PPG/10% dx
100% PPG/20% Fi
10% PEG/20% Fi
50% PAA/10% dx
50% PAA/10% Fi

Since the osmolarity of each of the polymers comprising the two-phase system varies with their concentrations, the volumes of the polymers after mixing will readjust to osmotic equilibrium if the two-phase polymer mixture is phase separated. This osmotic re-equilibrium may be exploited to concentrate solutes in one of the phases, as is desirable in the method according to the present invention. For example, PEG (m.w. 8000) has a higher osmolarity than dextran (m.w. 71,000) at comparable concentration. Therefore, the dextran phase tends to shrink after mixing these two polymers in a two-phase system. This so-called "sugar-based polymer shrinkage" (as illustrated by the PEG phase removing water from the dextran phase) depends on both the hydrocarbon-based polymer and the sugar-based polymer concentrations, as well as the initial hydrocarbon-based polymer/sugar-based polymer volume ratio.

To approximate the shrinkage, one can assume the osmolarity is a linear function of the concentration of polymers (which often is not exactly the case), and that at the same concentrations, the osmolarity of hydrocarbon-based polymer is M times that of sugar-based polymer (M is constant only if the linearity holds). Thus, in a two-phase mixture comprising PEG/dx, the osmotic equilibrium is reached through the volume change v from one phase to the other $$C_p V_p(V_d - v) = MC_d V_d(V_p + v) \tag{1}$$

where C and V, with subscripts p and d, are the concentrations and the initial volumes of PEG and dextran respectively. The sugar-based polymer shrinkage $v/V_d$ can than be expressed as:

$$v/V_d = (C_p - MC_d)/\{C_p + MC_d(V_d/V_p)\} \tag{2}$$

For each mixture of given initial concentrations of PEG and dextran, the shrinkage is more pronounced at low $V_d/V_p$ ratio. Since the linear relationship between concentration and osmolarity holds for neither dextran nor PEG, both equations (1) and (2) are not exact, and the values of M are not constant. Therefore, to get a more accurate approximation of sugar-based polymer shrinkage, an empirical curve can be determined for each mixture (See for example, FIG. 1).

It is possible to find mixtures such that the empirical $M \gg 1$ and at the limit of $V_p \gg V_d$, a high shrinkage ratio is obtained. Such mixtures are found in 10% PEG/15% dx and 10% PEG/20% dx. Generally for $V_d/V_p$ ratios of ½ to ⅕, the curves do not show appreciable shrinkage, but for ratios lower than ⅕, shrinkage goes up dramatically. It is also seen from the graph in FIG. 1, that for different PEG and dx concentrations, the percentage of shrinkage is different. For example, 20% PEG/15% dx and 20% PEG/20% dx combinations show a different behavior, since the values of M for these mixtures are different. It is possible to achieve a desired shrinkage for concentrating materials in the sugar-based polymer phase with a prior knowledge of the system.

Figure 2:
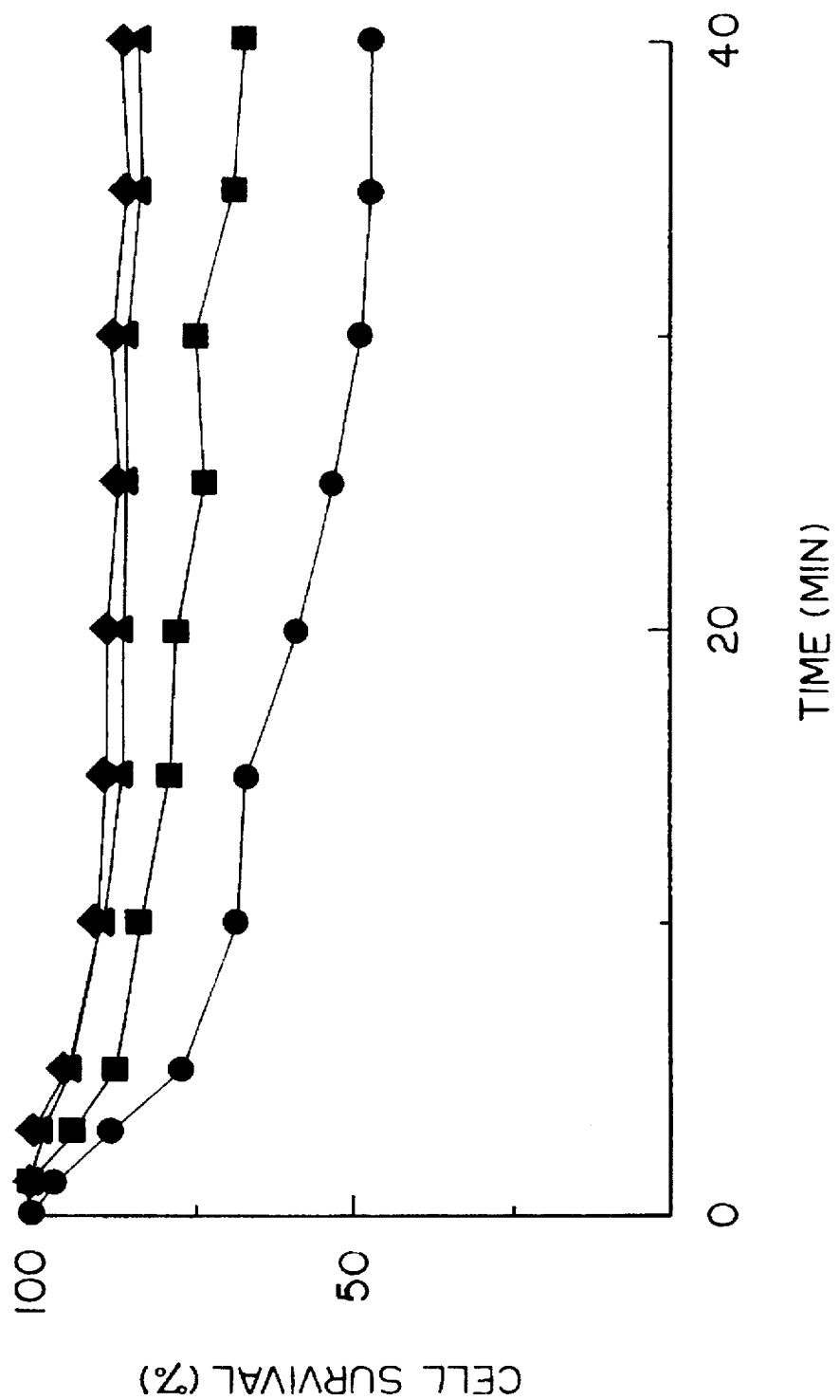
FIG. 2 is a graph of cell survival curves over time in different media. Circle, square, triangle and diamond symbols are for 25% dextran (m.w. 71000), 20% dextran (m.w. 71000), 10% PEG (m.w. 8000), and 10% PEG/20% dx, respectively.

While not the only hydrocarbon-based polymer that is useful in a combination comprising a two-phase polymer system in accordance with the present invention, PEG (m.w. 8000) is a preferred hydrocarbon-based polymer based on our observations and experience that PEG (m.w. 8000) appears to be the best choice for maintaining cell viability. Results of cell viability test in various polymer solutions are shown in FIG. 2. Cell viability in 10% or 20% PEG alone for more than one hour is very high. Viabilities in 15% and 20% dextran are similar when compared to each other, but lower than that in PEG solutions. In 25% dextran, the viability is poor. In a combination, the cell viability in 10% PEG/20% dx appears to be about the same as in 10% PEG alone.

Figure 3:
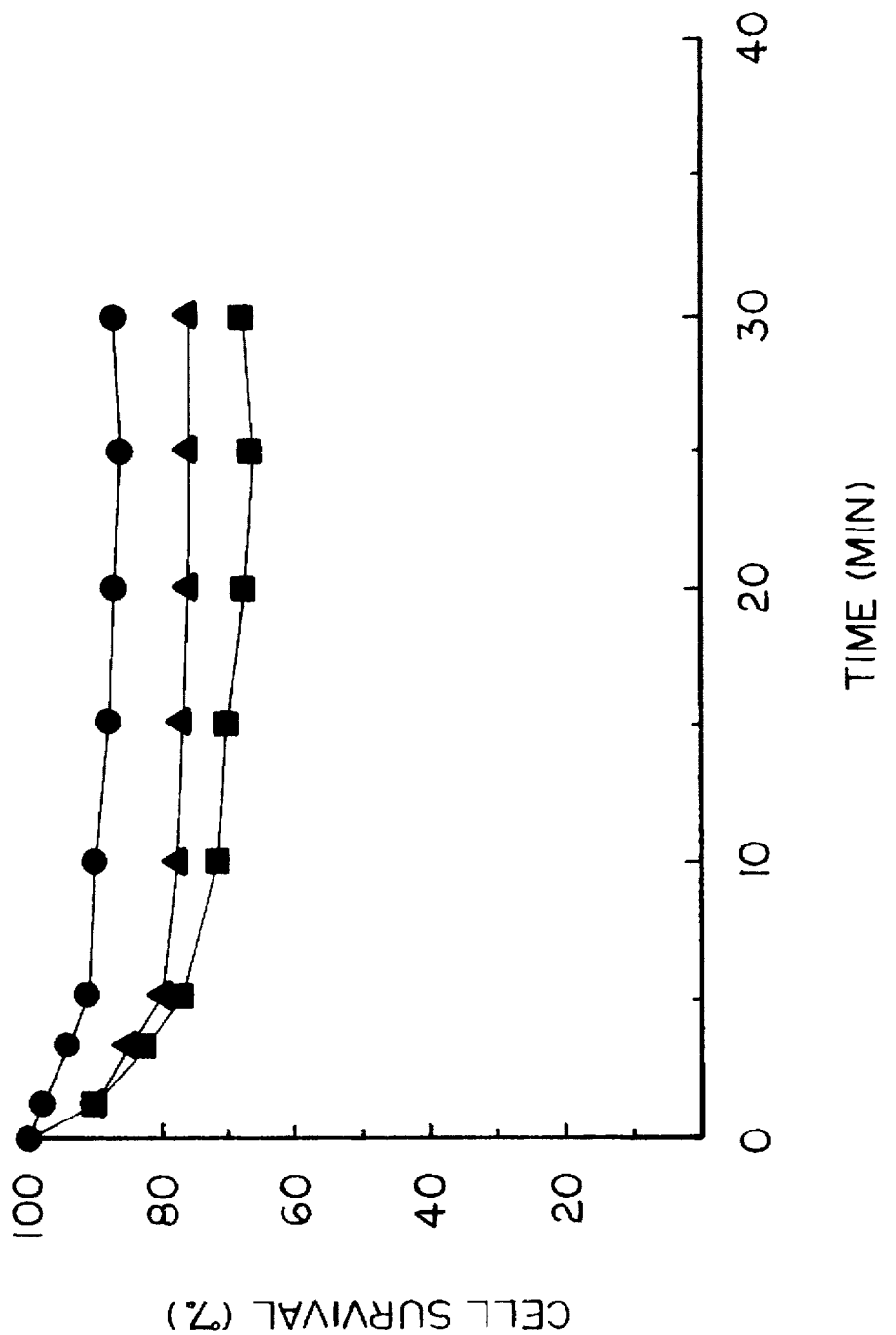
FIG. 3 is a graph of cell survival curves over time in one and two phase systems after subjecting to 3 exponential electric field pulses. Circle, square and triangle are for 10% PEG-20% dx, 20% PEG-20% dx and BSS (balanced salt solution) media, respectively.

Cell survival in two-phase polymer systems after electroporation was tested (FIG. 3). The survival rates in 10% PEG/20% dx and 20% PEG/20% dx mixtures are comparable to that in a balanced salt solution ("BSS" containing 125 mM NaCl, 5 mM KCl, 4 mM $CaCl_2.2H_2O$, 2.5 mM $MgCl_2.6H_2O$, and 5 mM Tris-HCl). Comparing viability curves of 10% PEG/20% dx in FIGS. 2 and 3, one can see that electroloading only reduces the cell viability slightly when this combination is used in a two-phase polymer system.

EXAMPLE 2
General loading protocol

For cell loading experiments, the loading biological material is mixed into the sugar-based polymer phase. The target cells may be suspended in either water soluble polymer phase; i.e., either the sugar-based polymer phase or the hydrocarbon-based polymer phase. Although the volume may vary depending on the combination of polymers used, generally the initial volume of the sugar-based polymer phase containing biological materials is usually set at about ⅛ of the total volume of the reaction mixture. The remaining volume of the reaction mixture may be the hydrocarbon-based polymer phase. The two-phase solution is then vortexed for a second to create an emulsion.

Figure 4A:
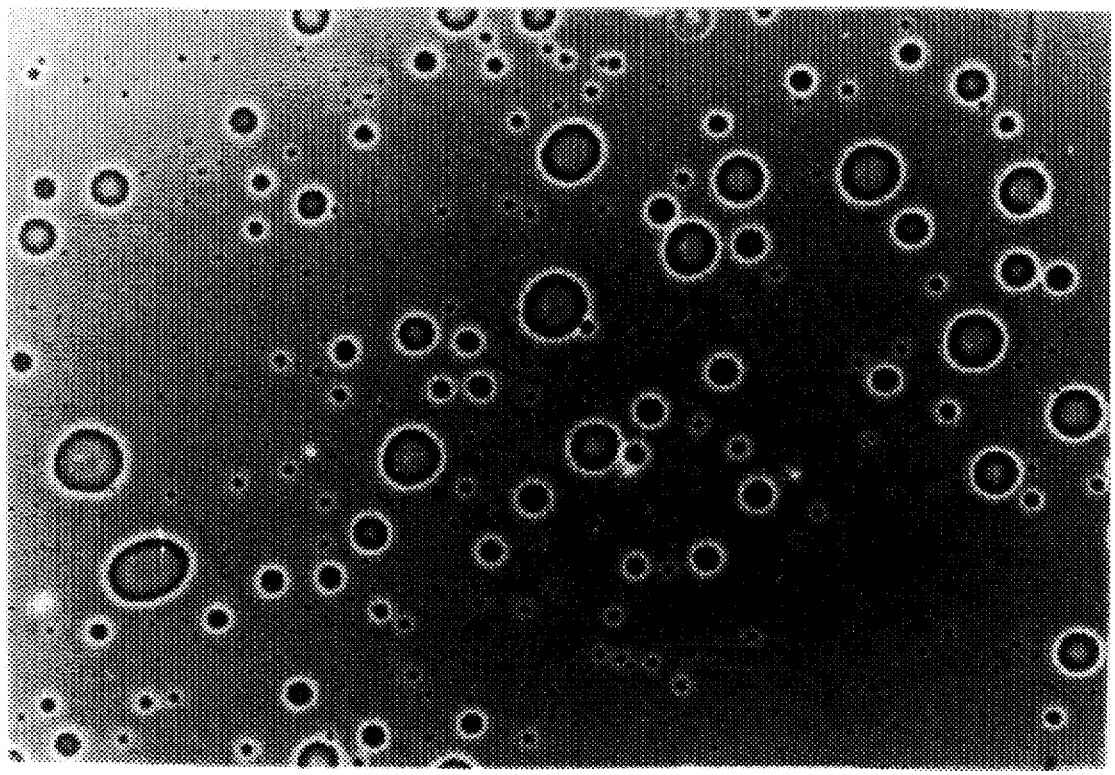
FIG. 4A illustrates an emulsion comprising PEG/dx as observed by optical microscopy.
Figure 4B:
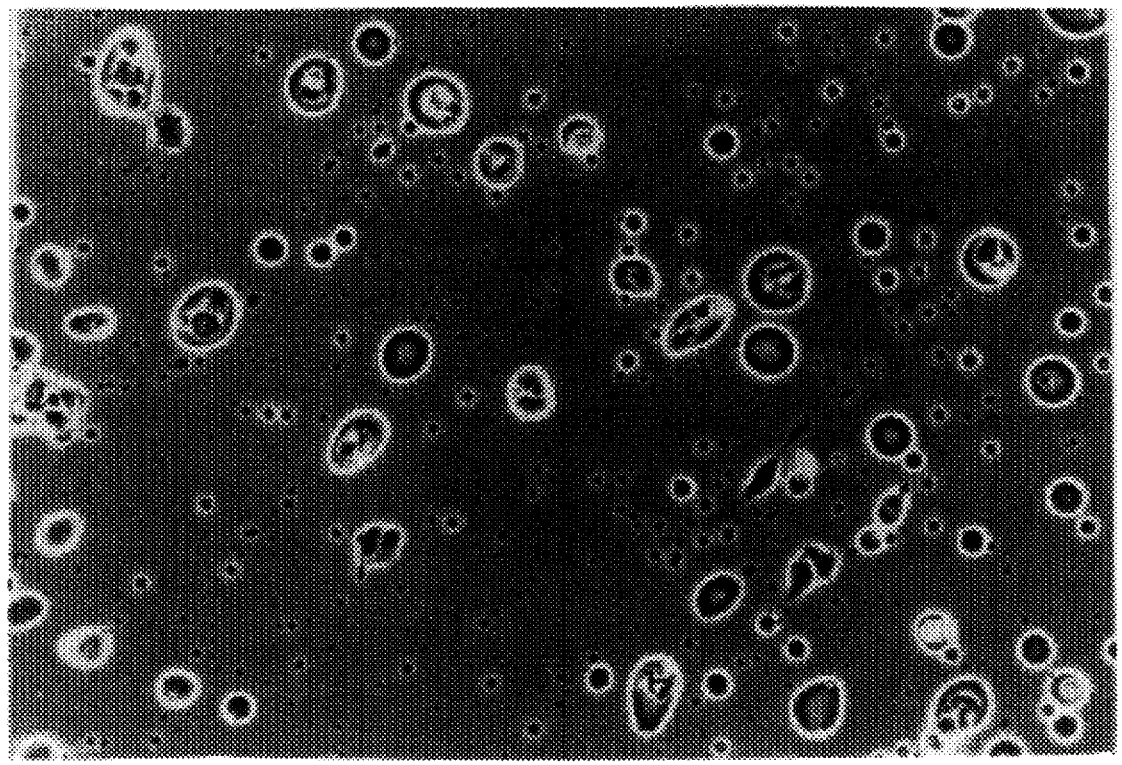
FIG. 4B illustrates an emulsion comprising PEG/dx and target cells and biological material, wherein the target cells and biological material are encapsulated in small droplets of dx suspended in the surrounding PEG.

Under an optical microscope, the sugar-based polymer phase containing target cells and biological material encapsulated in small droplets, suspended in the surrounding hydrocarbon-based polymer solution. For example, FIG. 4A illustrates an emulsion comprising PEG/dx. FIG. 4B illustrates an emulsion comprising PEG/dx and target cells and biological material, wherein the target cells and biological material are encapsulated in small droplets of dx suspended in the surrounding PEG. For most biological materials contained in media of various ionic strength up to BSS, or B+K medium (125 mM KCl, 15 mM NaCl, 1.2 mM $MgCl_2$, 3 mM glucose and 25 mM HEPES), the partition favors predominantly the sugar-based polymer phase. Fine partition adjustments may be made by changing the ionic strength in the various polymer solutions used.

The two-phase polymer system is then ready to be exposed to the pulsing electric field of the electroloading process. For example, electroporation of mammalian cells may be performed using one to three exponential electric pulses (field strength 0.5–2kV/cm, halftime 300–500 μs) generated by any exponential pulse generator. Rectangular pulses of comparable field strength and duration are equally effective. The samples containing the reaction mixture are typically placed in a narrow cuvette chamber with a volume capacity of 600 μl, and with the distance between the two parallel electrodes as 2.5 mm. The number of pulses, capacity, and the geometry of the pulse chamber is not critical, as long as the field-time integral is kept approximately constant.

Immediately after electroporation, the suspension may be re-separated into two bulk phases by centrifugation, or diluted directly from suspension with buffer solutions. For example, in transfection experiments involving mammalian cells, the treated target cell suspension may be transferred to a recovery medium (e.g., B+K medium containing 33% bovine serum) for 20 minutes. After that time, cells are washed and transferred either into BSS for further analysis or to cell culture medium for further growth. In cell loading experiments, the loaded target cells may be collected by centrifugation.

EXAMPLE 3
Loading neutral macromolecules of different molecular weights (FITC Dextran) into mammalian cells In this embodiment of the present invention, neutral macromolecules are loaded into mammalian cells using compositions and the method according to the present invention, and using methods outlined in Examples 1 and 2. Different molecular weights of dextran were labelled with fluorescein isothiocyanate (FITC), and then introduced into CHO cells by the method according to the present invention. For illustration purposes, a high molecular weight biological material (FITC-dextran m.w. 147,000) and a low molecular weight biological material (FITC dextran m.w. 3000) were used. Using $2 \times 10^6$ cells/ml and 30 μg/ml of FITC-dextran per sample, electroporation was done in the conventional suspension in balance salt solution (BSS), or in a two-phase system (10% PEG/20% dx) according to the method of the present invention. In the electroporation process, three exponential electric field pulses were applied. The loading efficiency was assayed by the amount of fluorescence in electroporated cells as determined by FACS (fluorescence-activated cell sorting).

Both the control (in BSS) and the two-phase samples were pulsed using the same setting of the pulse generator. The BSS sample has lower resistance than the two-phase polymer sample, therefore the pulse half time (=RC) is shorter. In the case of the high molecular weight biological material and at all field strengths, the best loading efficiency by the two phase system is at least twice, and up to 6, times that by the conventional system (Table 3A). In this experiment, the most effective two-phase system comprising a combination of PEG and dx is 10% PEG/20% dx and/or 10% PEG/15% dx. In order to differentiate the effects due to shorter pulse (lower resistance) from that due to two-polymer phase system, a separate experiment was carried out using identical pulse lengths in both cases. The result is shown in Table 3C. From these results, the higher loading appears to be due to the use of two-phase system according to the method of the present invention.

For the low molecular weight biological material and at high field strength (2 kV/cm), loading using the conventional method (e.g., in BSS) is not uniform. Two peaks are observed in the fluorescence histogram, indicating two populations of cells-one with very low fluorescence (about 40% of the cell population) and one with high fluorescence (about 60% of the cell population). Comparison of the loading using the conventional method with the best obtained using a two-phase system shows that loading with the two-phase system according to the method of the present invention is quite uniform, and the mean fluorescence is slightly less than that of the high loading population by the conventional method. In this experiment, the most effective two-phase system comprising a combination of PEG and dx is 10% PEG/20% dx. At a lower field strength (500 V/cm), both the conventional method and the two-phase system according to the method of the present invention give uniform loading. However, the method according to the present invention is 2.5 times more effective than the conventional method (Table 3B).

TABLE 3

| MEDIA | RELATIVE MEAN FLUORESCENCE Experiments | | | PULSE PARAMETERS |
|---|---|---|---|---|
| | 1 | 2 | 3 | |
| A. FITC-dextran (m.w. 147,000) | | | | |
| 10% PEG-20% dx | 80 | 90 | 105 | 2 kV/cm; 500 µs |
| BSS | 8/30 | 15 | 50 | 2 kV/cm; 300 µs |
| 10% PEG-15% dx | 100 | | | 2 kV/cm; 500 µs |
| 20% PEG-20% dx | 19 | | | 2 kV/cm; 500 µs |
| 20% PEG-10% dx | 28 | | | 2 kV/cm; 500 µs |
| 10% PEG-25% dx | 60 | | | 2 kV/cm; 500 µs |
| BSS | 50 | 50 | 9 | 0.5 kV/cm; 500 µs |
| 10% PEG-20% dx | 90 | 30 | | 0.5 kV/cm; 500 µs |
| 10% PEG-15% dx | | 25 | | 0.5 kV/cm; 500 µs |
| B. FITC-dextran (m.w. 3,000) | | | | |
| BSS | 20/120 | 20/115 | 25/140 | 2 kV/cm; 300 µs |
| 10% PEG-20% dx | 90 | 90 | 100 | 2 kV/cm; 500 µs |
| 10% PEG-25% dx | 70 | | | 2 kV/cm; 500 µs |
| 20% PEG-20% dx | 70 | | | 2 kV/cm; 500 µs |
| 20% PEG-10% dx | 40 | | | 2 kV/cm; 500 µs |
| BSS | 20 | 25 | | 0.5 kV/cm; 300 µs |
| 10% PEG-20% dx | 50 | | | 0.5 kV/cm; 500 µs |
| C. FITC-dextran (m.w. 147,000) | | | | |
| BSS | 12 | | | 2 kV/cm; 300 µs |
| 10% PEG-20% dx | 88 | | | 2 kV/cm; 300 µs |

EXAMPLE 4
Loading DNA into mammalian cells

In this embodiment of the present invention, nucleic acid molecules are loaded into mammalian cells using compositions and the method according to the present invention, and using methods outlined in Examples 1 and 2. DNA comprising type 7 Coliphage (m.w. $25 \times 10^6$) was labelled with propidium iodide (PI) using methods known in the art. 20 µg of PI-labeled DNA was used as the biological material to be introduced into CHO cells per electroporation sample. Cell suspensions ($2 \times 10^6$ cells/ml) in BSS or a two-phase polymer system, and containing the labeled DNA, were placed into respective cuvette chambers and pulsed with three exponential electric field pulses (2 kV/cm and 300 µs halftime). The results from DNA loading comparing the conventional method (BSS) with the method according to the present invention are shown in Table 4. Both high field strength (2 kV/cm) and low field strength (400 V/cm) pulses were used. In all experiments cell concentration and DNA concentration were the same. Data in Table 4 show that when high field strength pulses or low field strength pulses were used in DNA loading with the two phase system according to the method of the present invention, approximately 90% loading is observed. In sharp contrast, using the conventional electroporation method gives no more then 3% loading. In this experiment, the most effective two-phase system comprising a combination of PEG and dx is 10% PEG/20% dx. In additional control experiments, cells without DNA were electroporated, and subsequent to treatment, 20 µg labeled DNA was added to the cells. These cells were incubated for 5 minutes at room temperature, and then analyzed for fluorescence. No fluorescent cells were detected in such control experiments.

TABLE 4

| MEDIUM | % LOADING | | E. FIELD PARAMETERS |
|---|---|---|---|
| BSS | 3 | 3.6 | 1.8 kV/cm; 300 µs |
| 10% PEG/20% dx | 94 | 92 | 2 kV/cm; 500 µs |
| BSS | 0 | 0 | 0.4 kV/cm; 300 µs |
| 10% PEG/20% Dx | 87 | 89 | 0.4 kV/cm; 500 µs |

EXAMPLE 5
Transfecting vectors into mammalian cells 5.1 In this embodiment of the present invention, and using compositions and the method according to the present invention, and methods outlined in Examples 1 and 2, mammalian cells are transfected by a recombinant vector. In the transfection experiments, $10^6$ cells/ml and 5-20 µg of DNA are used per sample. The first transfection experiments were designed to test and compare the transfection efficiency of electroporation in a conventional method (in B+K medium); in a two-phase polymer system according to the method of the present invention; and a standard method using DEAE-dextran. The cells used were a COS cell line; and the recombinant vector used was pSV-B galactosidase vector. Transfection efficiency was measured by cell scoring using a commercially available staining kit for galactosidase activity. The results showing comparison of the various methods for transfection are illustrated in Table 5A. DEAE-Dextran and the conventional electroporation methods gave the same transfection efficiency when compared to each other. However, when those methods were compared to the method of the present invention using a two-phase polymer system, the method of the present invention was approximately 3 to 4 fold more effective.

5.2 It should be noted that this cell line (COS) is relatively easy to transfect, and thus, the advantage of the two-phase method may not be not fully appreciated. In contrast, Melan C immortalized melanocytes are very difficult to transfect, using conventional DEAE-Dextran method. Thus, this second set of transfection experiments were designed to test and compare the transfection efficiency of electroporation in a conventional method (in B+K medium); in a two-phase polymer system according to the method of the present invention; and a standard method using DEAE-dextran, using cells which are known to be difficult to transfect. The recombinant vectors used were tyrosinase cDNA (in pBK-RSV; total 6407 bp) and pSV-B galactosidase vector (containing an SV40 promoter and enhancer; total 6821 bp). Transfection efficiency was measured by cell scoring using a commercially available staining kit for galactosidase activity. The results showing comparison of the various methods for transfection are illustrated in Table 5B. Two field strengths (2 kV/cm and 0.5 kV/cm) were used. At either electrical setting, no significant transfection is detected by the conventional electroporation. No transfection was detected using the DEAE-dextran method. Only the method according to the present invention using a two-phase polymer system gave some transfection of a significant percentage.

5.3 A third set of transfection experiments were designed to test and compare the transfection efficiency of electroporation in a conventional method (in B+K medium); in a two-phase polymer system according to the method of the present invention; and a standard method of transfection using calcium phosphate ($CaPO_4$) and lipofectin; in lymphoid cells. The target cells comprised B lymphoid cells isolated from human peripheral blood. The recombinant vector used is pCP4 (10.4 kb) containing the fucosidase cDNA (2 kb) (pCEP4-fuc, total 12.4 kb). Transfection efficiency was measured by assaying for fucosidase activity. Alternatively, pCP4 was labeled with FITC, and the relative fluorescence from each transfection method was analyzed. The results showing comparison of the various methods for transfection, as measured by relative fluorescence, are illustrated in Table 5C. Three field strengths (2 kV/cm, 0.8 kV/cm and 0.5 kV/cm) were used. Transfection using calcium phosphate and lipofectin was unsuccessful. For all electric parameters tested, the method according to the present invention using a two-phase polymer system is at least 4 times more effective in transfection than electroporation in B+K medium. More significantly, the efficiency of the method according to the present invention using a two-phase polymer system does not decrease with lower pulse field strength in both the lymphocyte and the melanocyte transfections, and as depicted from the DNA loading experiment (Table 4).

This significant finding enables the user of the method according to the present invention to reduce the field strength needed for transfection. With reduced threshold voltages, significant advantages are conferred: (a) the electroloading method is safer for the user; (b) the cost of low voltage electroporation equipment and accessories may be lower; and (c) the present low voltage applications can be used for bacterial transformation, which usually demands higher voltages. An additional advantage conferred by the method according to the present invention, demonstrating a higher transfection efficiency rate than conventional methods, is its application to gene or cell therapy. Transfecting cells at a high efficiency is a requisite for gene delivery when only a limited number of cells are available. Therefore, the method according to the present invention may be valuable for in vitro gene therapy aiming at such target cells as human bone marrow cells.

TABLE 5

| MEDIUM | % CELL TRANSFECTED | | E. FIELD PARAMETERS |
|---|---|---|---|
| A. COS Cells | | | |
| (Percentage of transfected cells) | | | |
| DEAE-dextran Electroporation: | 4.6 | | |
| B + K MEDIUM | 3.7 | | 2 kV/cm; 300 μs |
| 10% PEG-20% dx | 13.9 | | 2 kV/cm; 500 μs |
| unpulsed control | 0.2 | | |
| B. Melanocytes | | | |
| Experiments | | | |
| | I | II | |
| DEAE-dextran Electroporation: | 0 | | |
| B + K MEDIUM | 0 | 0.1 | 2 kV/cm; 300 μs |
| 10% PEG-20% dx | 5.8 | 5.2 | 2 kV/cm; 500 μs |
| B + K MEDIUM | 0 | | 0.5 kV/cm; 300 μs |
| 10% PEG-20% dx | 6.0 | | 0.5 kV/cm; 500 μs |

TABLE 5-continued

| MEDIUM | % CELL TRANSFECTED | | | E. FIELD PARAMETERS |
|---|---|---|---|---|
| C. B-lymphoid cells | | | | |
| (Relative fluorescence) | | | | |
| Calcium phosphate Electroporation: | 0 | | | |
| B + K MEDIUM | 48 | | | 0.5 kV/cm; 300 μs |
| 10% PEG-20% dx | 1500 | | | 0.5 kV/cm; 500 μs |
| B + K MEDIUM | 430 | | | 2 kV/cm; 200 μs |
| 10% PEG-20% dx | 1600 | | | 2 kV/cm; 400 μs |
| B + K MEDIUM | 160 | | | 0.8 kV/cm; 200 μs |
| 10% PEG-20% dx | 1350 | | | 0.8 kV/cm; 400 μs |
| D. B-lymphoid cells | | | | |
| (intracellular/extracellular relative fucosidase activity) | | | | |
| Experiments | | | | |
| | I | II | III | |
| Calcium phosphate | 0 | | | |
| Lipofectin | 0 | | | |
| Electroporation: | | | | |
| B + K MEDIUM | 157/176 | | | 2 kV/cm; 250 μs |
| 10% PEG-20% dx | 378/444 | | | 2 kV/cm; 260 μs |
| B + K MEDIUM | 24/26 | | | 1 kV/cm; 246 μs |
| 10% PEG-20% dx | 97/131 | | | 1 kV/cm; 258 μs |
| B + K MEDIUM | | 102/203 | | 1.8 kV/cm; 240 μs |
| 10% PEG-20% dx | | 199/338 | | 1.2 kV/cm; 256 μs |
| B + K MEDIUM | | 136/273 | | 1.2 kV/cm; 280 μs |
| 10% PEG-20% dx | | 256/450 | | 1.2 kV/cm; 260 μs |
| B + K MEDIUM | | | 145/120 | 2 kV/cm; 256 μs |
| 10% PEG-20% dx | | | 458/385 | 2 kV/cm; 256 μs |

In subsequent experiments, the field strength and pulse length parameters for both the method according to the present invention (two-phase) and the conventional method (one phase) were optimized for human B lymphoid cells using pCEP4-fuc. The optimal transfection efficiency of the method according to the present invention was consistently approximately three times that of the conventional method, as illustrated in Table 5D. The optimal parameter for field strength and pulse (field strength×pulse half time) for transfection of B lymphoid cells using the method according to the present invention is about 1 kV msec/cm, which is much less than the optimal parameter for the conventional method.

Additionally, another significant finding was observed. Expression of fucosidase by B lymphoid cells transfected according to the method of the present invention was monitored over a period of six months of continuous passage. While there was a slow and gradual decline of fucosidase activity, surprisingly there still remained 10% of fucosidase activity at the end of the monitoring period. This is believed to be the longest known retainment of activity observed in this particular cell line.

Additional mammalian cell lines have been similarly, and successfully, transfected using the method and compositions according to the present invention. For example, EBV-lymphoma cells have been transfected with either the method according to the present invention or the conventional method. It was also observed that this cell line cannot be transfected by CaPO$_4$ and lipofectin methods. Using the method according to the present invention, a transfection efficiency of 8.5% was observed with a parameter of 1.1 kV/cm and 0.28 msec pulses. In contrast, using the conventional method only a transfection efficiency of 2% was observed with a parameter of 2 kV/cm and up to 0.4 msec pulses.

EXAMPLE 6
Electrofusion of cells

In this embodiment of the present invention, compositions and the method according to the present invention, and the methods outlined in Examples 1 and 2, were used. The method according to the present invention having a two-phase polymer system can also be used to facilitate electrofusion. The current practice of electrofusion of cells is to use dielectrophoresis to form "pearl chains" of cells, so that cells are in contact when the fusing pulse is applied. Alternative methods to form cell-cell contacts prior to the application of fusing pulses are being developed by us. These methods have the advantages of being simpler and more effective, eliminating the use of the AC field, thereby cutting the complexity of equipment. The maximal fusion yield of CHO cells using these methods is about 45% viable fusion.

Figure 5:
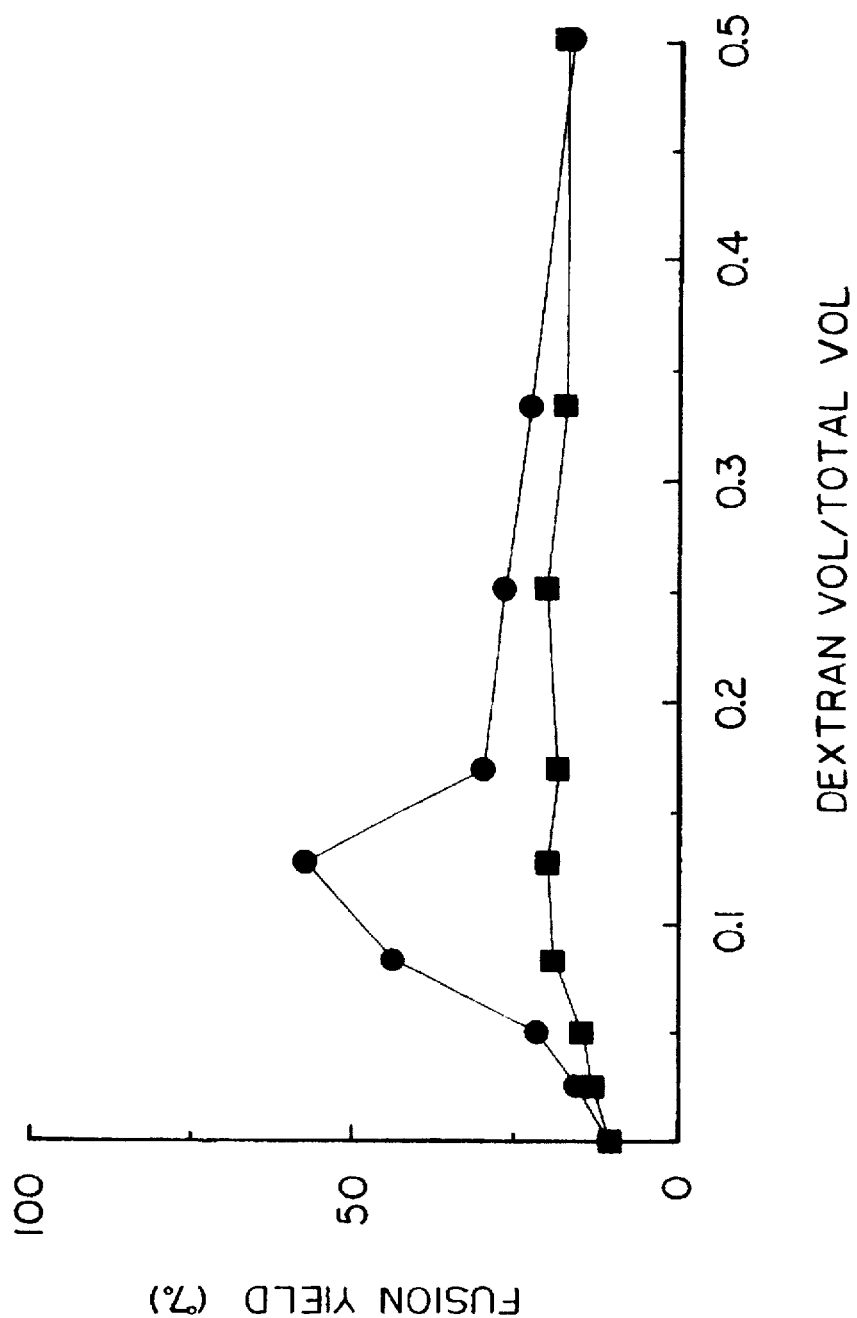
FIG. 5 is a graph plotting electrofusion yield of CHO cells in 10% PEG-20% dx suspension, as a function of the initial dextran volume fraction of the mixture. Circles and squares represent samples of cells initially placed in dextran and PEG phases, respectively.

Electrofusion of CHO cells in 10% PEG/20% dx was measured as a function of the initial dextran/PEG volume ratio (Vd/VP). Cells were placed initially in either dextran or PEG phase, and suspended in a vortexed emulsion. A single 4 kV/cm and 0.72 msec half time exponential electric pulse was applied to the suspension to induce fusion. The percentage of fusion was obtained by microscopic counting of syncytia. FIG. 5 shows the fusion yield of both samples as a function of the dextran volume fraction. Fusion yield is much higher if cells are first placed in the dextran phase. A peak in fusion yield (60%) is found at the dextran volume fraction of 0.13. At a low ratio of 0.08, the fusion yield (45%) is equivalent to that in 10% PEG solution alone, indicating a maximum cell-cell contact that is equivalent to that in 10% PEG is reached. Lower yield at lower dextran volume fraction ratio may imply adverse effects of dextran at the extreme shrinkage condition. Higher dextran volume ratios than 0.13 give lower fusion yield, indicating that the dextran volume shrinkage may not sufficient to induce good cell-cell contact.

The fact that the electrofusion yield in a two-phase system according to the present invention is higher than that in pure PEG solution appears to signify a fusion-promotive and/or lysis-protective effect of the phase boundary. The high fusion field and versatility of this two-phase aggregation method according to the present invention is applicable to cell-membrane-vesicle and cell-liposome fusion. Thus, the method may be useful for receptor insertion onto cell surfaces, as well as drug and gene delivery into cytoplasm with high efficiency.

EXAMPLE 7
Transformation of bacterial cells

Figure 6A:
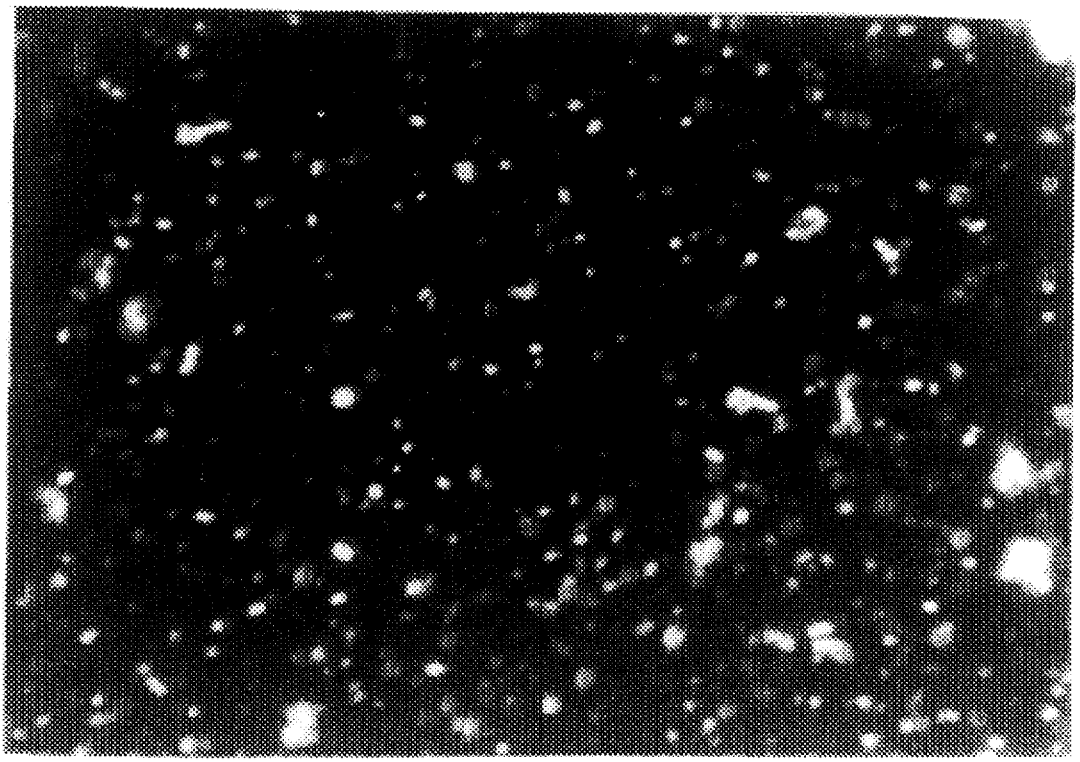
FIG. 6A shows the maximum fluorescence intensity of a bacterial sample electroloaded with the method according to the present invention.
Figure 6B:
FIG. 6B shows the maximum fluorescence intensity of a bacterial sample electroloaded with a conventional method.

In this embodiment of the present invention, compositions and the method according to the present invention, and the methods outlined in Examples 1 and 2, were used to load and transfect *Escherichia coli*. The biological material to be loaded was recombinant vector pCMV-βgal. The same concentration of bacterial cells (5 µl of a 1 O.D. suspension) and recombinant vector (10 µg) were used to electroporate by the conventional (single phase) method and were added together to the isotonic sucrose solution used. In the method according to the present invention, *E. coli* (competent DH5-α) were added to the hydrocarbon-based polymer phase (10% PEG) and the recombinant vector was added to the dx phase (20% dx). A series of pulse field strengths and duration were used to determine desirable parameters. After pulse and wash, the respective bacterial samples with maximum fluorescence by either of the methods was compared. The maximum fluorescence intensity of the sample treated with the method according to the present invention (see FIG. 6A) was about 5 times that of the conventional method (See FIG. 6b). Under these conditions, and using the method according to the present invention, the best loading efficiency appears to occur at 4.5 kV/cm, with 3 pulses of 7 msec each. Such parameters are much milder than the parameters for conventional electroporation methods which require 10 kV/cm pulse fields for bacterial loading.

It should be understood that while the invention has been described in detail herein, the examples were for illustrative purposes only. Other modifications of the embodiments of the present invention that are obvious to those of ordinary skill in the art of molecular and cellular biology, biophysics, and related disciplines are intended to be within the scope of the appended claims.

We claim:

1. A composition for electroloading biological material into target cells, said composition comprises a two-phase polymer system having a first phase containing a first water soluble polymer to which is added the cells that are to be electroporated, said first water soluble polymer is selected from the group consisting of polyethylene glycol having a molecular size between 600 daltons and 20,000 daltons, and polypropylene glycol having a molecular size of 4,000, and a second phase containing a second water soluble polymer containing the biological material to be electroloaded into the cells; or where in said first phase no cells to be electroloaded are present, but where said second phase contains both the cells and biological material; said second water soluble polymer is selected from the group consisting of dextran having a molecular size ranging from greater than 9,000 daltons to 249,000 daltons, and Ficoll having a molecular weight of 400,000 daltons; wherein interfacial energy and osmotic control of the first and second polymer phases are such that upon mixing of said phases effect shrinkage in volume of one of said phases, and wherein target cells and biological material added to the system with subsequent mixing are encapsulated in a concentrated form in a suspension containing both the first water soluble polymer and the second water soluble polymer for electroporation.

2. The composition according to claim 1, wherein the osmotic control of the first and second polymer phases comprises one of said polymers in the two-phase polymer system having a higher osmolarity than the other polymer, resulting in shrinkage in volume of said other polymer in the two-phase polymer system.

3. The composition according to claim 1, wherein the first and second water soluble polymers possess, with respect to target cells or biological materials, the properties of biocompatibility, and nontoxicity.

4. The composition according to claim 1, wherein the concentrations of the first water soluble polymer and the second water soluble polymer limit post-electrical pulse colloidal osmotic swelling, and effect influx of biological material into target cells.

5. The composition according to claim 1, wherein the two-phase polymer system has a total volume where one-fifth to one-tenth of the total volume is a sugar-based polymer, and the remainder of the total volume is a hydrocarbon-based polymer.

6. The composition according to claim 1, wherein the first polymer is polyethylene glycol in a concentration between 5% and 25% w/w.

7. The composition according to claim 1, wherein the first polymer is polypropylene glycol in a concentration of 100% w/w.

8. The composition according to claim 1, wherein the second polymer is dextran in a concentration ranging between 10% and 25% w/w.

9. The composition according to claim 1, wherein the second polymer is FICOLL in a concentration ranging from 10% to 25% w/w.

10. The composition according to claim 1, wherein the first polymer is polyethylene glycol in a concentration in a range of 5% to 25% w/w; and wherein the second polymer is dextran in a concentration in a range of 10% to 25% w/w.

11. A method for electroloading biological material into target cells, comprising the steps of:
   (a) mixing the biological material into the phase containing the second polymer set forth in claim 1;
   (b) mixing the target cells into the first polymer phase or the second polymer phase;
   (c) mixing the first polymer phase with the second polymer phase to create an emulsion wherein target cells and biological material are encapsulated in a concentrated form in a suspension containing both the first water soluble polymer and the second water soluble polymer;
   (d) exposing the emulsion to a pulsing electric field; and
   e) thereby obtaining cells containing electro loaded biological material.

12. The method according to claim 11, wherein the biological material comprises a biomolecule selected from the group consisting of a protein, a polysaccharide, a drug, and a dye.

13. The method according to claim 12, wherein the biological material is a protein.

14. The method according to claim 13, wherein the protein is an enzyme.

15. The method according to claim 12, wherein the biological material is a polysaccharide.

16. The method according to claim 15, wherein the polysaccharide is a polynucleotide.

17. The method according to claim 16, wherein the polynucleotide is DNA.

18. The method according to claim 16, wherein the polynucleotide is RNA.

19. The method according to claim 16, wherein the polynucleotide is contained in a vector.

20. The method according to claim 11, wherein the target cells comprise a cell type selected from the group consisting of bacterial cells, and animal cells.

21. The method according to claim 20, wherein the animal cells are mammalian cells.

22. The method according to claim 21, wherein the mammalian cells are isolated human cells.

23. The method according to claim 11, wherein the reaction has a volume where one-fifth to one-tenth of the volume is comprised of a sugar-based polymer, and the remainder of the volume is comprised of a hydrocarbon-based polymer.

24. The method according to claim 11, wherein the first polymer is polyethylene glycol in a concentration ranging from 5% to 25% w/w.

25. The method according to claim 11, wherein the first polymer is polypropylene glycol in a concentration of 100% w/w.

26. The method according to claim 11, wherein the second polymer is dextran in a range of 10% to 25% w/w.

27. The method according to claim 11, wherein the second polymer is FICOLL in a range of 10% to 25% w/w.

* * * * *

UNITED STATES PATENT AND TRADEMARK OFFICE
CERTIFICATE OF CORRECTION

PATENT NO.   : 5,789,213
DATED        : August 4, 1998
INVENTOR(S)  : Sek Wen Hui, et al It is certified that error appears in the above-indentified patent and that said Letters Patent is hereby corrected as shown below:

Column 14, line 32 - delete "upon"

Column 14, line 32 - delete "effect" and insert --effects--

Signed and Sealed this

Twenty-ninth Day of December, 1998

Attest:

BRUCE LEHMAN

*Attesting Officer*          *Commissioner of Patents and Trademarks*